United States Patent [19]
Kwan

[11] Patent Number: 5,564,924
[45] Date of Patent: Oct. 15, 1996

[54] HEXAGONAL ABUTMENT IMPLANT SYSTEM

[76] Inventor: Norman H. Kwan, 209 Indian Valley Trail, Mississauga, Ontario, Canada, L5G 2K5

[21] Appl. No.: 391,662

[22] Filed: Feb. 21, 1995

[51] Int. Cl.[6] .................................................. A61C 8/00
[52] U.S. Cl. ..................................... 433/173; 433/175
[58] Field of Search ................................... 433/172, 173, 433/175

[56] References Cited

U.S. PATENT DOCUMENTS

| | | | |
|---|---|---|---|
| 4,293,302 | 10/1981 | Hassler et al. | 433/173 |
| 4,511,336 | 4/1985 | Hidaka et al. | 433/173 |
| 4,955,811 | 9/1990 | Lazzara et al. | 433/173 |
| 4,988,298 | 1/1991 | Lazzara et al. | 433/173 |
| 5,049,072 | 9/1991 | Lueschen | 433/173 |
| 5,169,308 | 12/1992 | Kvist | 433/172 |
| 5,195,892 | 3/1993 | Gersberg | 433/173 |
| 5,322,443 | 6/1994 | Beaty | 433/173 |
| 5,344,457 | 9/1994 | Pilliar et al. | 433/175 |
| 5,462,436 | 10/1995 | Beaty | 433/173 |

*Primary Examiner*—Paul J. Hirsch
*Attorney, Agent, or Firm*—Howard J. Greenwald

[57] ABSTRACT

A dental implant assembly containing an integrally-formed abutment which has a top section, a bottom section integrally joined to the top section, and a passageway extending through these sections. The passageway is formed by a series of sixed stepped bores which initially decrease in size and then increase in size. The top section of the abutment has a cross-sectional shape substantially like a polygon; the shape is formed by alternating linear and arcuate walls.

17 Claims, 18 Drawing Sheets

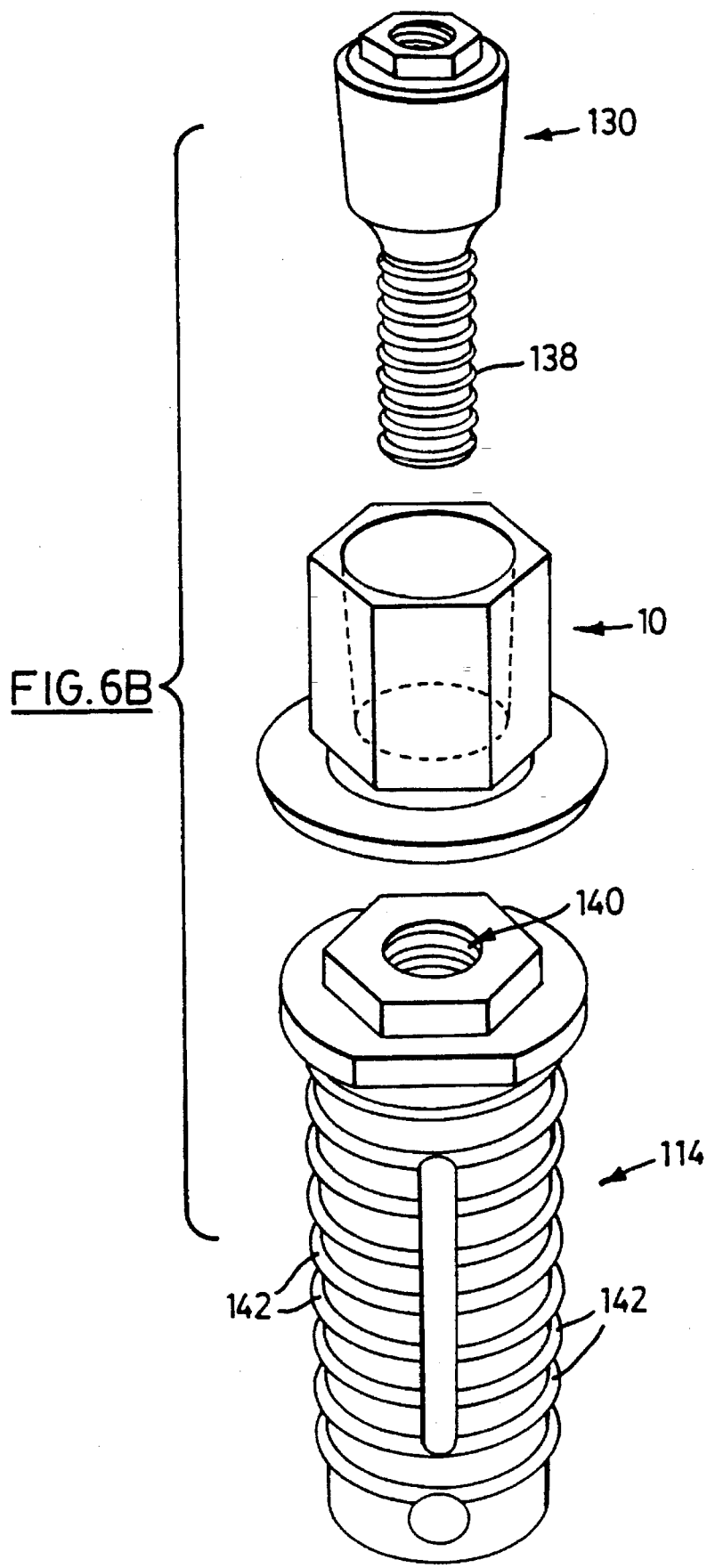

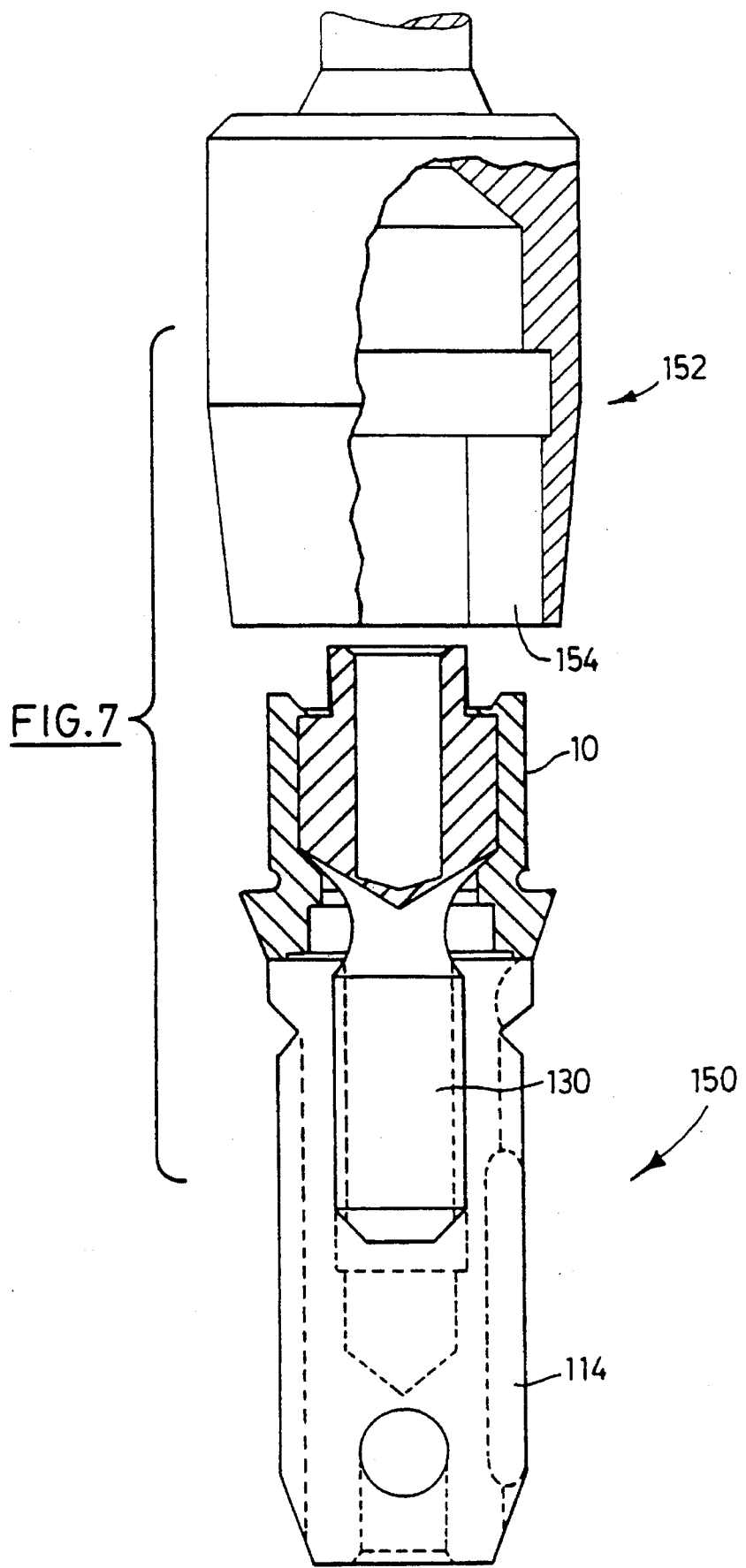

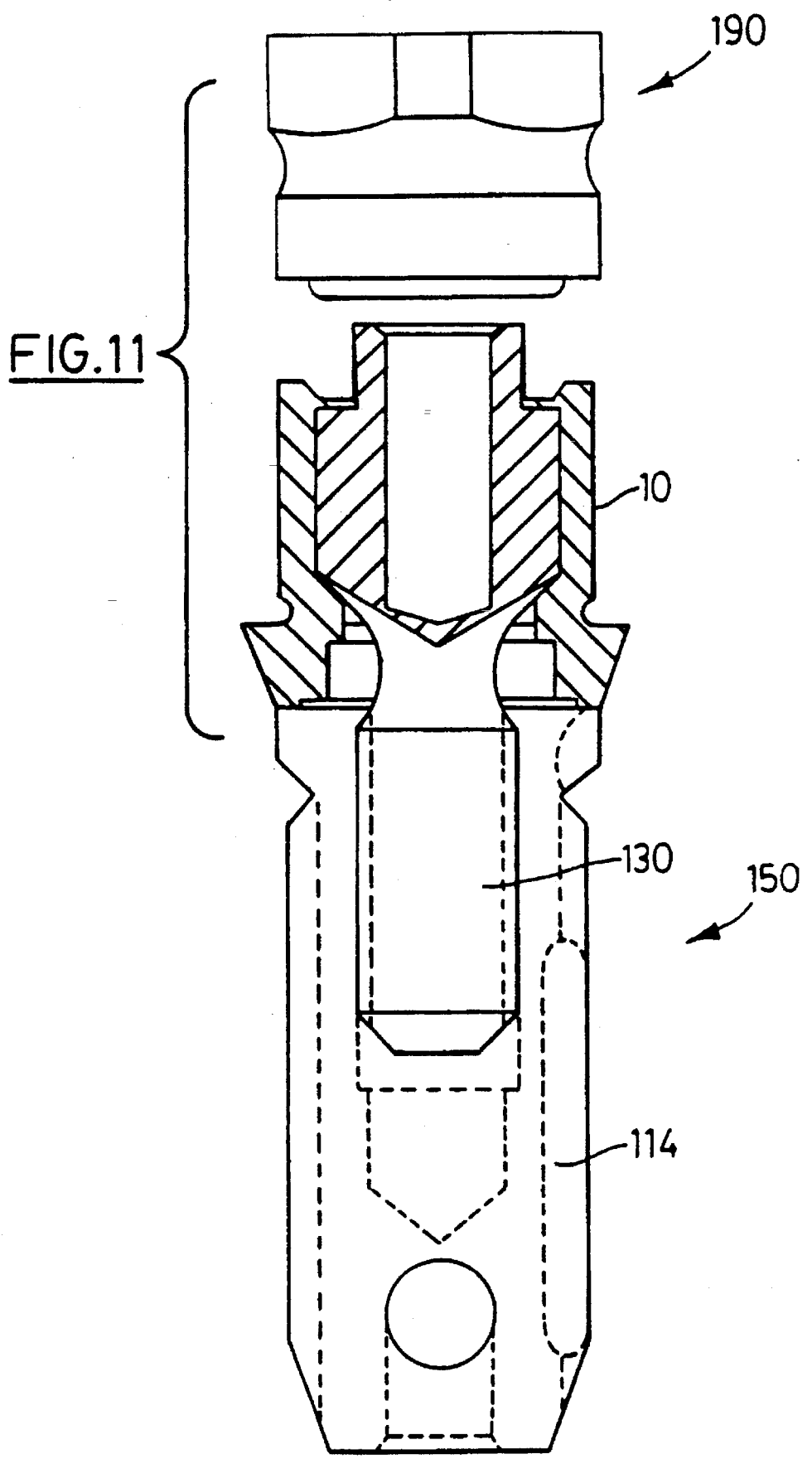

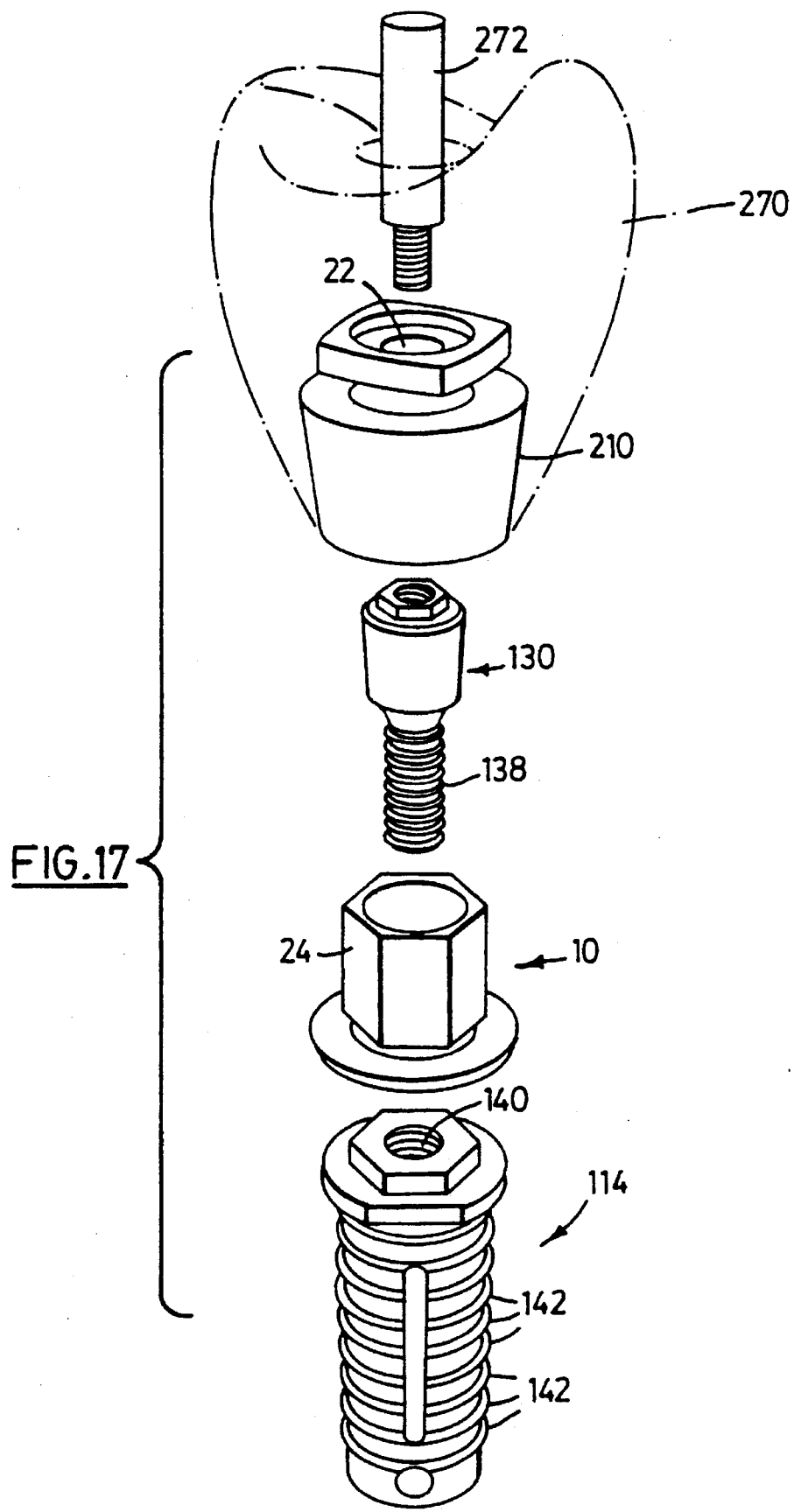

HEXAGONAL ABUTMENT IMPLANT SYSTEM

FIELD OF THE INVENTION

A dental implant abutment to which a dental implant may be fastened.

BACKGROUND OF THE INVENTION

Dental implants have been known, and used, since at least the 1930's; see, e.g., U.S. Pat. No. 5,312,254 of Joel L. Rosenlicht. See also U.S. Pat. No. 5,145,371 of Lars Jorneus which discusses the osseointegration method of integrating a dental implant into a patient's jaw. The disclosure of each of these patents is hereby incorporated by reference into this specification.

Dental implants are moderately expensive. It often costs from about three to four thousand dollars to implant a tooth into a patient's mouth.

One of the reasons for this substantial cost is the multiplicity of steps required by the implant procedure. These prior art steps will be described below with reference to Nobelpharma catalog PRI 385 94.03 2nd edition (published by the Nobelpharma AB, Box 5190, S-402 26 Goteborg, Sweden).

In the first step of the prior art procedure, an implant or "fixture" is purchased; see, e.g., page 7 of the Nobelpharma catalog and the reference to the 3.75 mm and 4.0 mm titanium fixtures illustrated on such page.

The fixture so purchases must then be placed into an "instrument set for fixture placement", which is shown on page 22 of the Nobelpharma catalog.

Once the fixture is disposed in the "instrument set . . .", a "fixture mount" is then attached to the fixture by means of a wrench and a screwdriver. The "fixture mount" devices are shown on page 22 of the Nobelpharma catalog. The instruments for fixture placement of the fixture are also shown on page 22 of the Nobelpharma catalog (see wrench part 17 and screwdriver part 19).

Thereafter, a "connection to contra-angle handpiece" (see part 11 on page 22 of the Nobelpharma catalog) is attached to a handpiece (see page 31 of the Nobelpharma catalog); and the implant assembly may then be driven into the jawbone of a patient.

Thereafter, the fixture mount is removed from the fixture. Thereafter, a cover screw (see page 9 of the Nobelpharma catalog) is inserted into the fixture. Thereafter, the surgical site is allowed to heal for from about 3 to about 6 months. See, e.g., Branemark/Zarb/Alberektsson: "Tissue Integrated Prostheses" (Quintessence Books, 1985).

After the healing period, the implant is exposed by surgical procedures, and the cover screw is removed. Thereafter, a healing abutment (see page 39 of the Nobelpharma catalog) is attached to the fixture. It generally is left in place for from about two to about three weeks, depending upon how the patient's tissue has healed.

Thereafter, the healing abutment is then removed, and a implant abutment is then attached to the fixture. The type of implant abutment to be used will depend on the requirements of the patient. Thus, e.g., and referring to pages 38 and 39 of the Nobelpharama catalog, one may standard abutment, and "EsthetiCone" abutment, a "CeraOne" abutment, a "Ball Attachment", an "Angulated Abutment", and the like.

Thereafter, the desired prosthesis is formulated by conventional means. Once the prosthesis has been prepared, it is fitted to the patient's mouth secured to the implant.

It will be apparent that this prior art procedure requires a myriad number of prosthetic instruments and parts, many trips by the patient to the dentist, and a several surgical procedures. Not only is the process tedious and expensive, but each surgical procedure introduces a certain element of risk, pain, and suffering.

It is an object of this invention to provide a process for implanting a prosthesis in a patient's mouth which is substantially less expensive, safer, and less-time consuming than the prior art procedures.

It is another object of this invention to provide a novel dental abutment.

It is yet another object of this invention to provide a novel carrier for such abutment.

It is yet another object of this invention to provide a novel healing ball which may be used with the abutment of this invention.

It is yet another object of this invention to provide a novel O-ring attachment system for securing dentures within a patient's mouth.

It is yet another object of this invention to provide a a novel gold cylinder which may be used with the abutment of this invention.

It is yet another object of this invention to provide a novel bar clip attachment system for securing a denture within a patient's mouth.

It is yet another object of this invention to provide a novel fixed, detachable implant supported bridge.

It is yet another object of this invention to provide a novel gold coping device for use with the implant abutment of this invention.

It is yet another object of this invention to provide a process for attaching a prosthesis to a patient which process is substantially more accurate than prior art processes.

SUMMARY OF THE INVENTION

In accordance with this invention, there is provided a novel abutment which is preferably an integrally-formed, sleeve-shaped element containing a lower portion and an upper portion. The exterior of the lower portion of the abutment contains an annular groove disposed between its base and the main, substantially polygonal portion of the abutment body. The sleeve of the abutment preferably contains rounded corners which are compatible with the oral tissue and its functions in the patient's mouth.

BRIEF DESCRIPTION OF THE DRAWINGS

The present invention will be more fully understood by reference to the following detailed description thereof, when read in conjunction with the attached drawings, wherein like reference numerals refer to like elements, and wherein:

FIG. 6B is an exploded perspective view illustrating how the retaining screw of FIG. 6A may be attached to an abutment and an implant fixture.

FIG. 7 is an exploded view an abutment implant assembly being driven into bone;

FIG. 11 is a sectional view of a the abutment/implant system being connected to a standard gold cylinder.

FIG. 17 is a an exploded perspective view illustrating how the gold coping device may be attached within a tooth and secured to the abutment.

DESCRIPTION OF THE PREFERRED EMBODIMENTS

Figure 1:
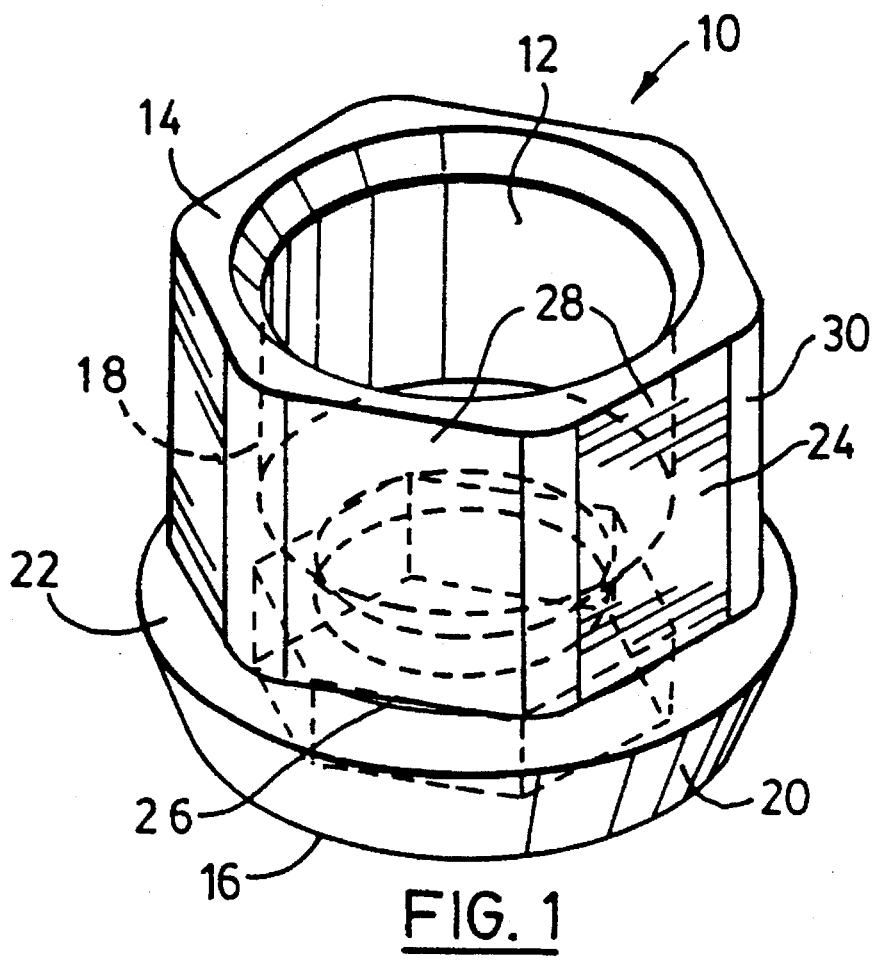
FIG. 1 is a perspective view of one preferred abutment of this invention.

Referring to FIG. 1, a perspective view of one preferred abutment 10 is shown. This abutment 10 is preferably an integral structure which consists or consists essentially of titanium or titanium alloy. Alternatively, the abutment 10 may consist of gold, silver, palladium, vanadium, cobalt alloy, stainless steel, and the like.

Any of the titanium or titanium alloy materials used in implants may be used to make abutment 10. Thus, by way of illustration and not limitation, one may use one or more of the materials disclosed in U.S. Pat. No. 5,373,621 (a titanium/aluminum/vanadium alloy), U.S. Pat. No. 5,372,660 (a titanium/zirconium alloy), U.S. Pat. Nos. 5,358,529, 5,354,390 (a titanium-base microalloy containing at least 98 weight percent of titanium), U.S. Pat. No. 5,334,264 (a nitrided titanium material), U.S. Pat. No. 5,326,362 (a titanium/aluminum/vanadium alloy), U.S. Pat. No. 5,205,921 (a coated titanium implant), U.S. Pat. No. 5,192,323 (a titanium/aluminum/vanadium alloy), and the like. The disclosure of each of these United States patents is hereby incorporated by reference into this specification.

In one preferred embodiment, abutment 10 is machined from pure titanium which, preferably, is originally in the form of a rod. It is preferred that the titanium used meet the standards set forth in A.S.T.M. Standard F 67-88, "Specification for Unalloyed Titanium for Surgical Implant Applications." In general, it is also preferred that the material used, regardless of whether it is titanium, titanium alloy, and/or other material, meet the requirements set forth in A.S.T.M. Standard Test F 981-87 "Practice for Assessment of Compatibility of Bio Materials (Non-Porous) for Surgical Implants".

Figure 2:
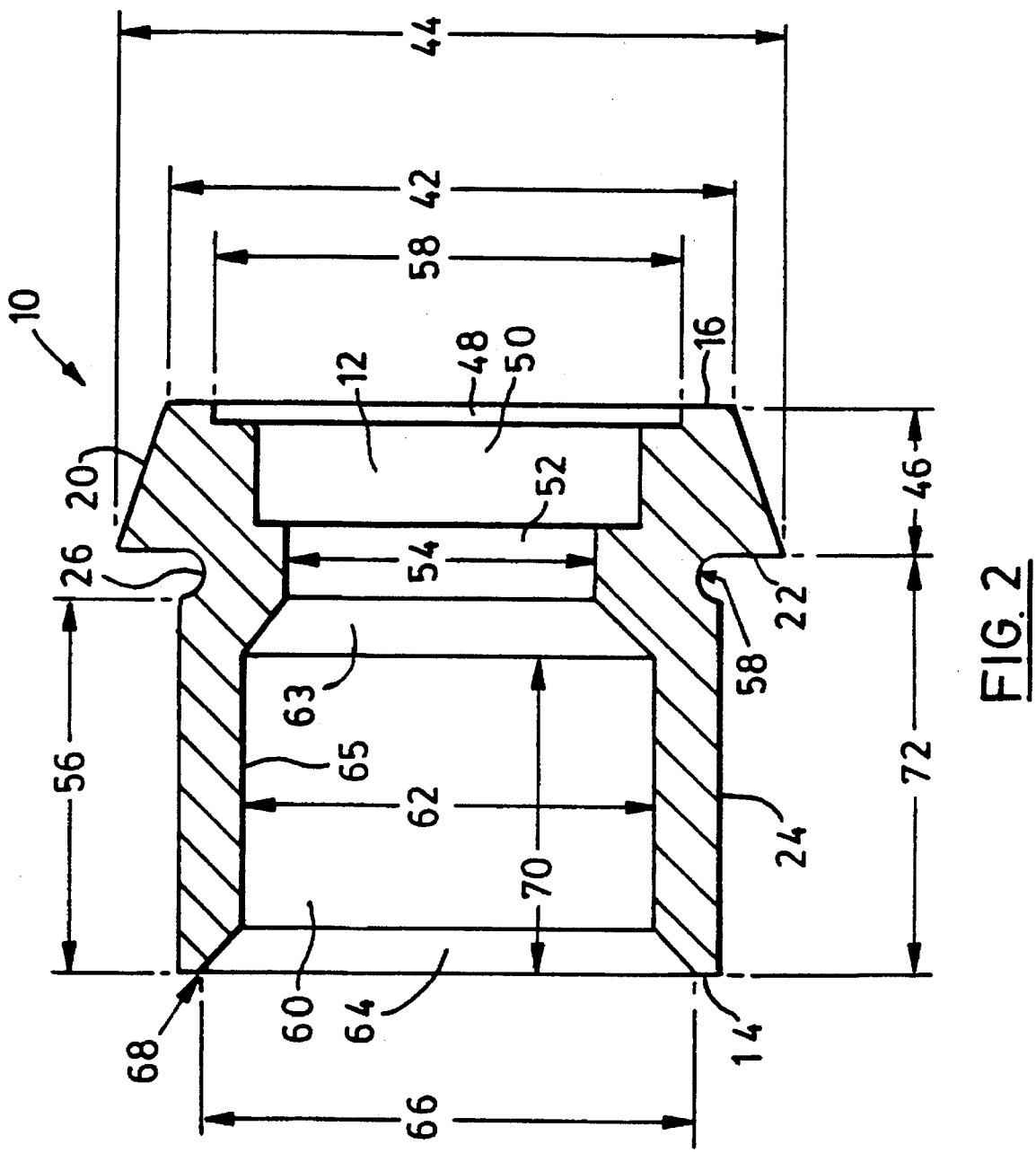
FIG. 2 is a sectional view of the abutment of FIG. 1.

Referring again to FIG. 1, it will be seen that abutment 10 is comprised of a hollow core 12 which extends from the top 14 of abutment 10 to its bottom (not shown in FIG. 1, but see bottom 16 in FIG. 2). The hollow core 12 is indicated in FIG. 1 by dotted line 18.

Referring again to FIG. 1, it will be seen that abutment 10 is comprised of a base 20 is extends upwardly and outwardly from its bottom 16 to form an intermediate ledge 22.

FIG. 2 better illustrates the preferred structure near ledge 22. It will be seen that, in the preferred embodiment illustrated, ledge 22 is disposed beneath substantially hexagonal portion 24 of abutment 10. Disposed between substantially hexagonal portion 24 and ledge 22 is annular groove. Without wishing to be bound to any particular theory, applicant believes that this structure provides a more secure attachment to devices attachable to abutment 10.

Referring again to FIG. 1, and in the preferred embodiment depicted therein, it seen that the substantially hexagonal portion preferably has rounded corners. This is also illustrated in FIG. 1A, which is a partial top view of the structure of FIG. 1.

Figure 1A:
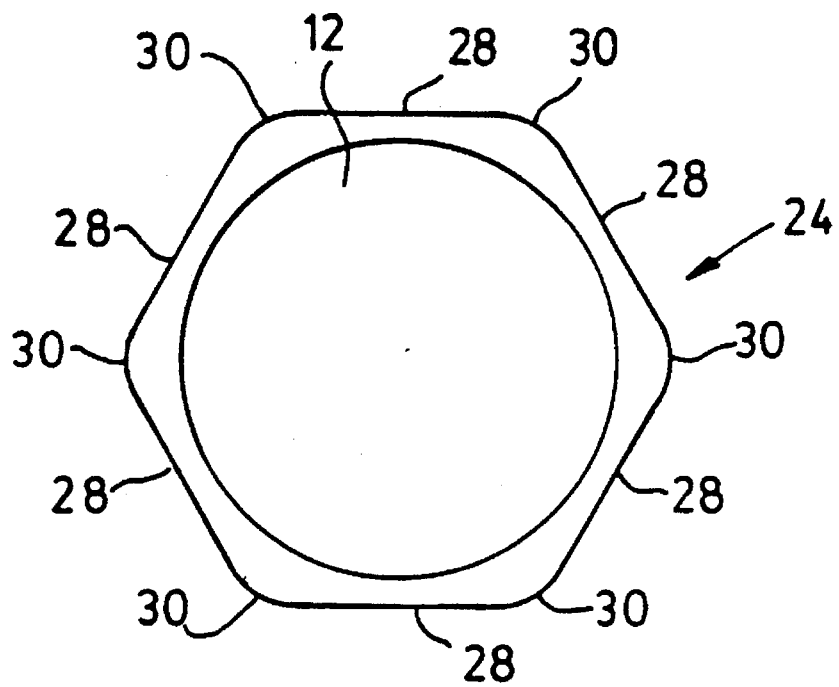
FIG. 1A is a top view of an abutment with a substantially hexagonal exterior shape.

Referring to FIG. 1A, it will be seen that hexagonal portion 24 is comprised of exterior surface which contains alternating linear portions 28 and arcuate portions 30. Without wishing to be bound to any particular theory, it is believed that the rounded corners (arcuate portions 30) in this structure are substantially compatible with the patient's mouth. Thus, e.g., these rounded corners do not irritate the patient's tongue during eating as much as the sharp corners present on normal hexagonal structures.

It is preferred that the length of each linear portion 28 be substantially equal to the length of each of the other linear portions 28. In one embodiment, the substantially hexagonal shape depicted in FIG. 1 is substantially symmetrical.

It is also preferred that the length of each linear portion 28 be at least about 1.2 times as long as the length of each curved portion 30. In one preferred embodiment, the length of each linear portion 28 is at least about 3.0 times as great as the length of each curved portion 30.

Figure 1B:
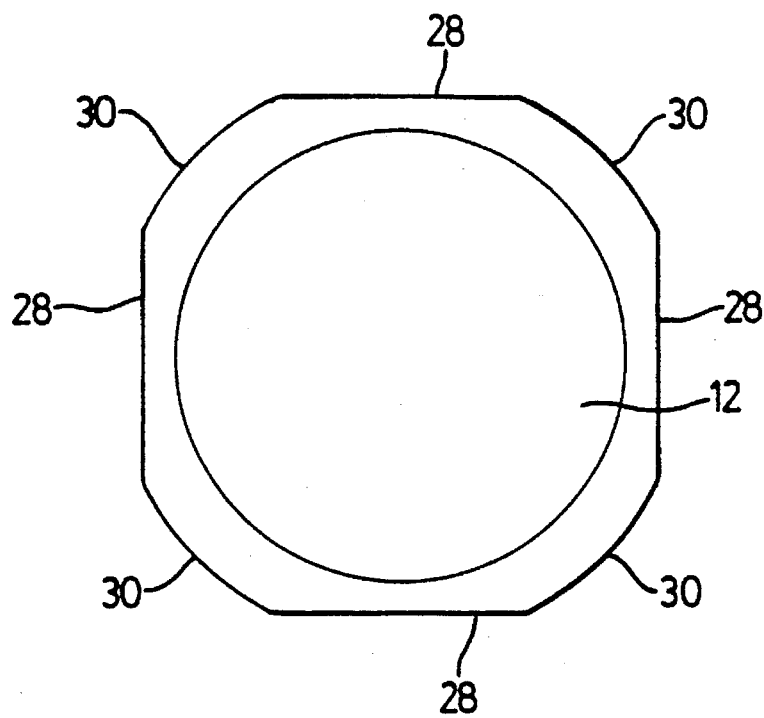
FIG. 1B is a top view of an abutment with a substantially square exterior shape.
Figure 1C:
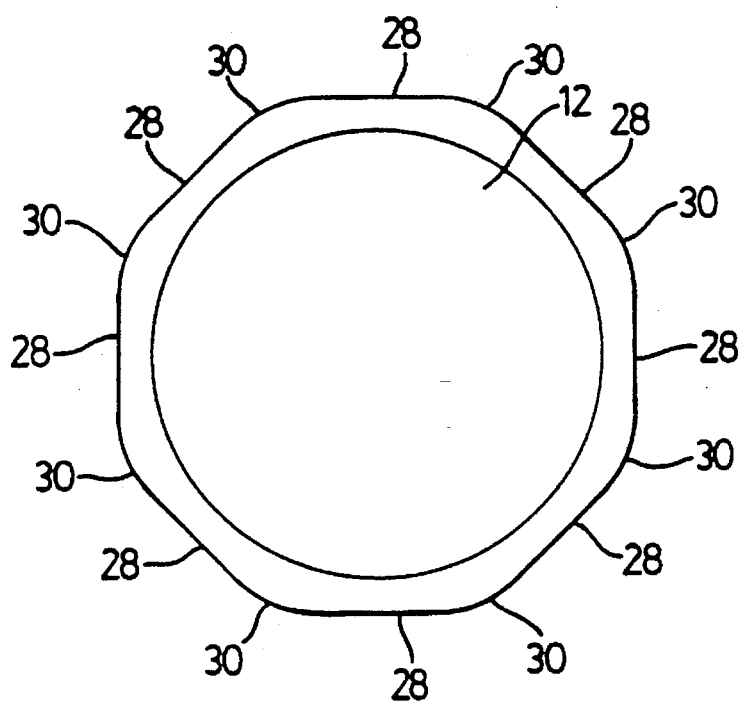
FIG. 1C is a top view of an abutment with a substantially octagonal exterior shape.

As will be apparent to those skilled in the art, the abutment 10 may have an exterior shape which need not be substantially hexagonal but may assume the shape of other polygons. Thus, FIG. 1B depicts a substantially share cross-sectional shape. Thus, FIG. 1C depicts a substantially octagonal cross-sectional shape.

As will be apparent to those skilled in the art, substantially any polygonal shape can be used which is capable of being mechanically engaged. Thus, by way of further illustration, one may use substantially triangular shapes, substantially pentagonal shapes, substantially heptagonal shapes, substantially nonagonal shapes, and the like. What is required of any such shape, however, is that contain alternating linear and non-linear sections (the latter preferably being arcuate) and that, preferably, they define a shape which is symmetrical along at least one axis of symmetry.

FIG. 2 is a sectional view of the abutment 10 of FIG. 1. Referring to FIG. 2, it will be seen that the base 20 of abutment 10 preferably has a width 42 at its bottom which is substantially less than its width 44 at its top. In general, width 44 is at least about 1.1 times as great as width 42. In one preferred, width 44 is 4.7 millimeters, and width 42 is 4.0 millimeters.

Referring again to FIG. 2, it will be seen that base 20 has a depth 46 which, preferably, is from about 0.5 to about 7.0 millimeters and, more preferably, is from about 0.5 to about 1.5 millimeters. In the preferred embodiment illustrated in FIG. 2, depth 46 is 1.0 millimeter.

Referring again to FIG. 2, it will be seen that, near base 20, hollow core 12 is comprised of stepped bores 48, 50, and 52.

Stepped bore 52 has a diameter 54 sufficient for a screw (not shown) to pass through it. In the preferred embodiment illustrated in FIG. 2, stepped bore 52 has a diameter 54 of 2.2 millimeters.

Referring again to FIG. 2, it will be seen that substantially hexagonal portion 24 extends from the top 14 of abutment 10 to annular groove 26. It is preferred that the distance 56 between top 14 and annular groove 26 of abutment 10 extend at least about 55 percent of the entire height of abutment 10. In one preferred embodiment, distance 56 is about 3.0 millimeters.

It is preferred that annular groove 26 have a substantially circular shape and, more preferably, have a radius of curvature 58 of from about 0.1 to about 0.2 millimeters. In one preferred embodiment, the radius of curvature of groove 26 is about 0.15 millimeters.

Referring again to FIG. 1, and in the preferred embodiment depicted therein, bore 48 has a diameter 59 of about 3.5 millimeters, bore 60 has a diameter 62 of about 3.0 millimeters, bore 64 has a diameter 66 at its top most point of about 3.5 millimeters, the distance 70 between point 68 and the end of bore 60 is 2.0 millimeters, and the distance between surface 68 and ledge 22 is 3.0 millimeters.

Figure 3:
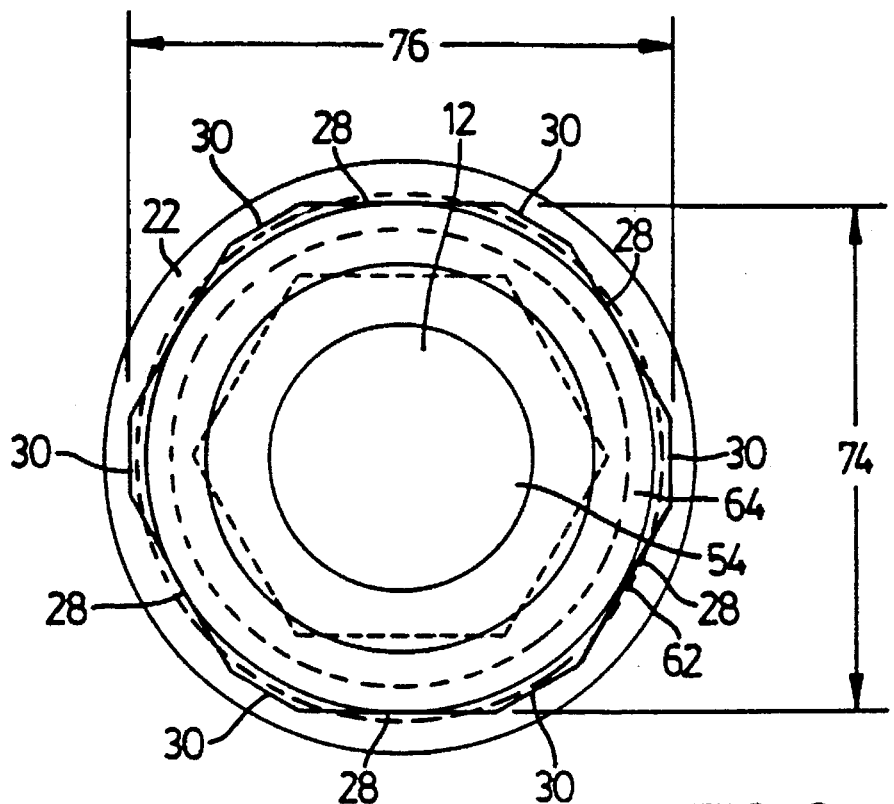
FIG. 3 is a top view of the abutment of FIG. 1.

FIG. 3 is a top view of abutment 10. In the preferred embodiment depicted in FIG. 3, the distance 74 between opposite linear surfaces on the exterior of the hexagonal sleeve preferably is about 3.9 millimeters; and the distance 76 between opposite arcuate surfaces on the exterior of the hexagonal sleeve is about 4.1 millimeters.

Figure 4:
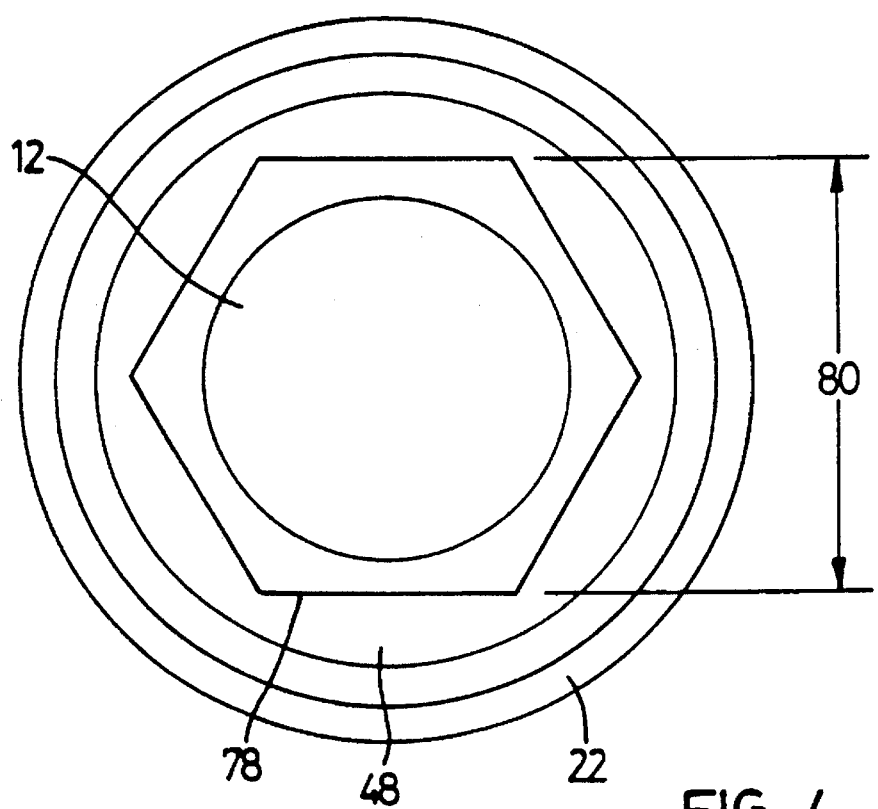
FIG. 4 is a bottom view of the abutment of FIG. 1.

FIG. 4 is a bottom view of abutment 10. Referring to FIG. 4, and in the preferred embodiment depicted therein, it will be seen that bore preferably has a substantially hexagonal cross-sectional shape 78 which is adapted to mate with the external hexagonal shape of the upper portion of an implant fixture (not shown). In the preferred embodiment shown, the distance 80 between opposing linear walls of said hexagonal shape is preferably 2.7 millimeters.

Referring again to FIG. 2, it will be seen that bore 63 is disposed between bore 60 and bore 52 and has diameter which continually decreases from bore 60 to bore 52, thereby forming a chamfered surface. It is preferred that said chamfered surface form an obtuse angle (as measured with respect to the interior wall 65 of bore 60) of from about 120 to about 150 degrees.

Figure 5:
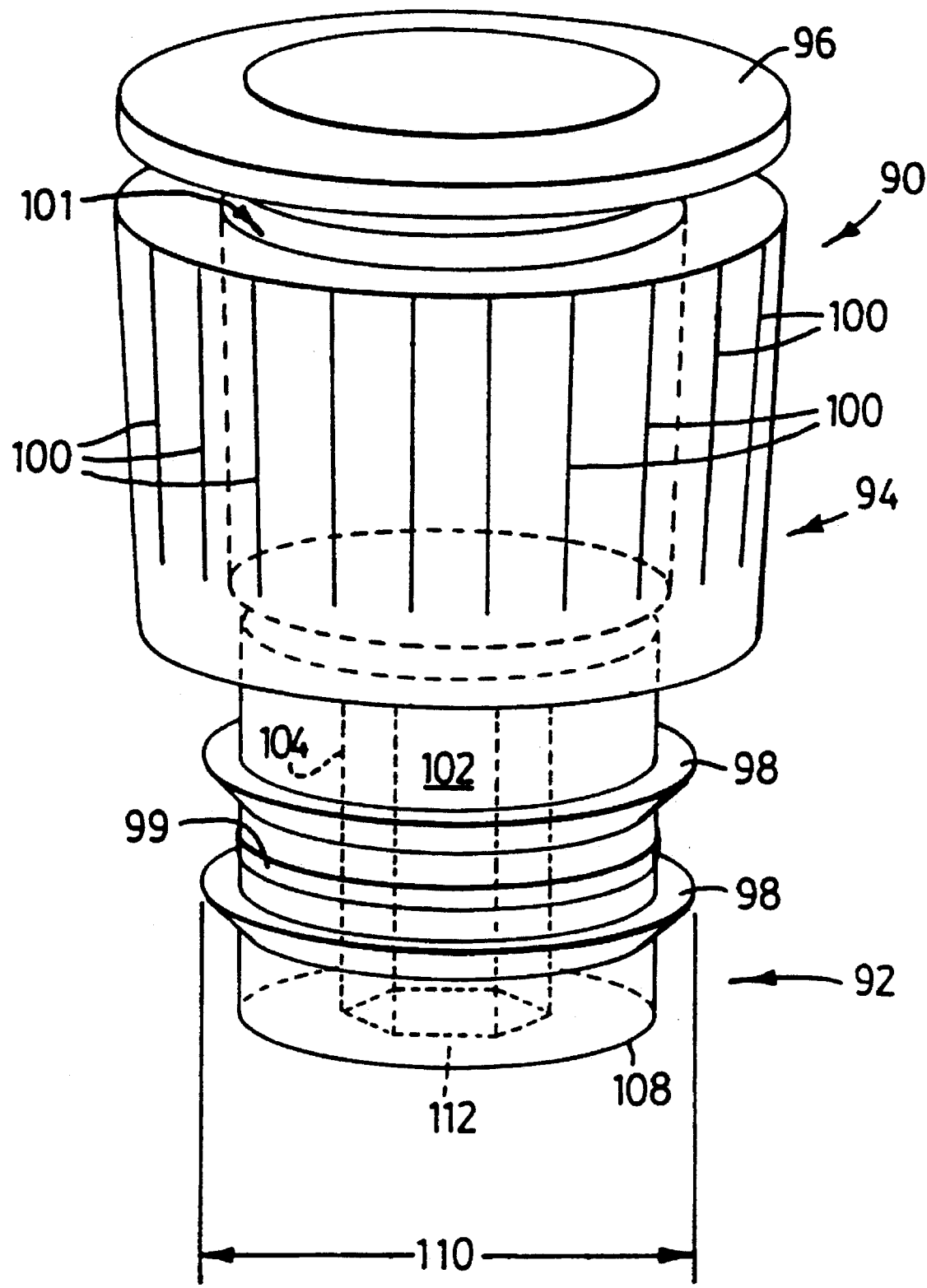
FIG. 5 is a perspective view of a carrier adapted to be used with the abutment of FIG. 1.

FIG. 5 is a perspective view of carrier 90 which is adapted to be removably connected to abutment 10 and to manually deliver it into the jaw of a patient.

Referring to FIG. 5, it will be seen that carrier 90 is preferably an integral assembly which, preferably, consists essentially of plastic material which, preferably, is non-toxic and thus is "medical grade".

One may use any of the "medical grade" material known to those skilled in the art such as, e.g., the plastics described in U.S. Pat. No. 5,356,709 (polypropylene copolymyer; styrene/ethylene/butylene/styrene copolymer), U.S. Pat. No. 5,312,251 (medical grade ceramic material), U.S. Pat. No. 5,326,364 (medical grade ceramic), and the like. The disclosure of each of these United States patents is hereby incorporated by reference into this specification.

In one preferred embodiment, carrier 90 consists essentially of high density polypropylene which is extruded into the desired shape.

Referring again to FIG. 5, it will be seen that carrier 90 is comprised of a fin 92, grip 94, and removable cover 96. The fin 92 is comprised of external annular ridges 98 which are adapted to fit within and be contiguous with a shipping vial (not show in FIG. 5). The grip 94 is preferably comprised of a multiplicity of vertically-extending ridges 100 which facilitate the handling of grip 94; and will be apparent to those skilled in the art, other means of facilitating the handling of grip 94 (such as, e.g., roughened surfaces) may also be used.

Within grip 94 is a compartment 101 in which an accessory part (not shown) may be stored. Removable cover 96 is adapted to snap into place within such compartment 101.

In one embodiment, removable cover 96 is color coded to indicate which part it is to be used in connection with.

A bore 102 (shown in outline by dotted line 104) extends from the top 106 of fin 92 to the bottom 108 of fin 92. That portion of bore 102 extending through fin 92 has a substantially hexagonal cross-sectional shape and, thus, is adapted to fit over and engage with the substantially hexagonal portion 24 of abutment 10.

In one preferred embodiment, illustrated in FIG. 5, the width 110 of fin 92 is about 9.9 millimeters, and maximum dimensional of the hexagonally shaped bore 102 as it exits fin 92 is about 4 millimeters.

In the preferred embodiment illustrated FIG. 5, the bottom surface 112 of the carrier 90 is preferably a flat surface adapted to mesh with the flat surface of ledge 22 (see FIGS. 1, 2, and 6) so that the carrier 90 is properly aligned with abutment 10 when it is removably connected thereto.

Figure 6:
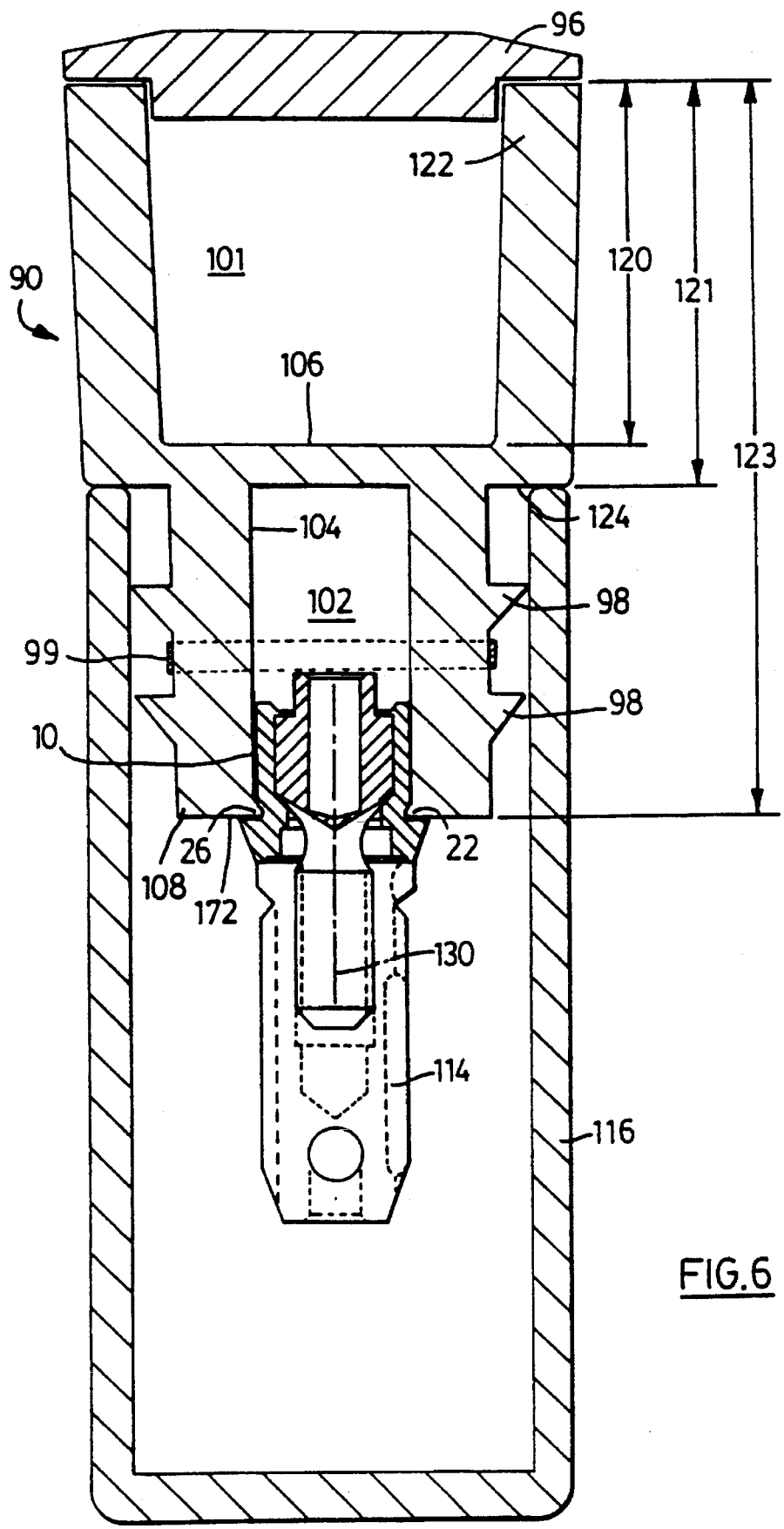
FIG. 6 is a sectional view of the carrier of FIG. 5 connected to the abutment of FIG. 1, which in turn is connected to an implant fixture, the whole assembly being disposed within a vial.

FIG. 6 is a sectional view of carrier 90 connected to abutment 10 which, in turn, is connected to implant fixture 114, the abutment and implant being disposed within a vial 116.

Referring to FIG. 6, and in the preferred embodiment illustrated therein, it will be seen that carrier 90 is removable connected to both cover 96, vial 116, and abutment 10, all by a friction fit. The entire assembly may be disposed in another vial (not shown). In this embodiment, the depth 120 of compartment 101 is preferably from about 5 to about 10 millimeters, the distance 121 between the top lip 122 and the bottom surface 124 of the grip 90 is from about 6 to about 12 millimeters, and the distance 123 from the top of carrier 90 to its bottom is from about 10 to about 20 millimeters.

Referring again to FIG. 6, it will be seen that the carrier 90/abutment 10/vial 16 assembly may be used in conjunction with an implant fixture 114. This assembly is quite adaptable and may be used with substantially any of the implant fixtures known to those skilled in the art.

Thus, by way of illustration and not limitation, one may use one or more of the implant fixtures disclosed in U.S. Pat. Nos. 5,338,197, 5,061,181, 5,030,095, 4,960,381, 4,932,868, 4,871,313, 4,854,873, 4,854,872, 4,713,004, 4,468,200, 4,330,891, 4,016,651, 3,672,058, 3,579,831, 2,609,604, 5,376,004, 5,364,268, 5,362,235, 5,302,125, and the like. The disclosure of each of these United States patents is hereby incorporated by reference into this specification.

By way of further illustration, and referring to the Nobelpharma catalog referred to elsewhere in this specification, one may use any of the implant fixtures disclosed on page 7 of such catalog.

Referring again to FIG. 6, it will be seen that implant fixture 114 is preferably connected to abutment 10 by means of retaining screw 130. The retaining screw 130 is shown in more detail in FIG. 6A.

Figure 6A:
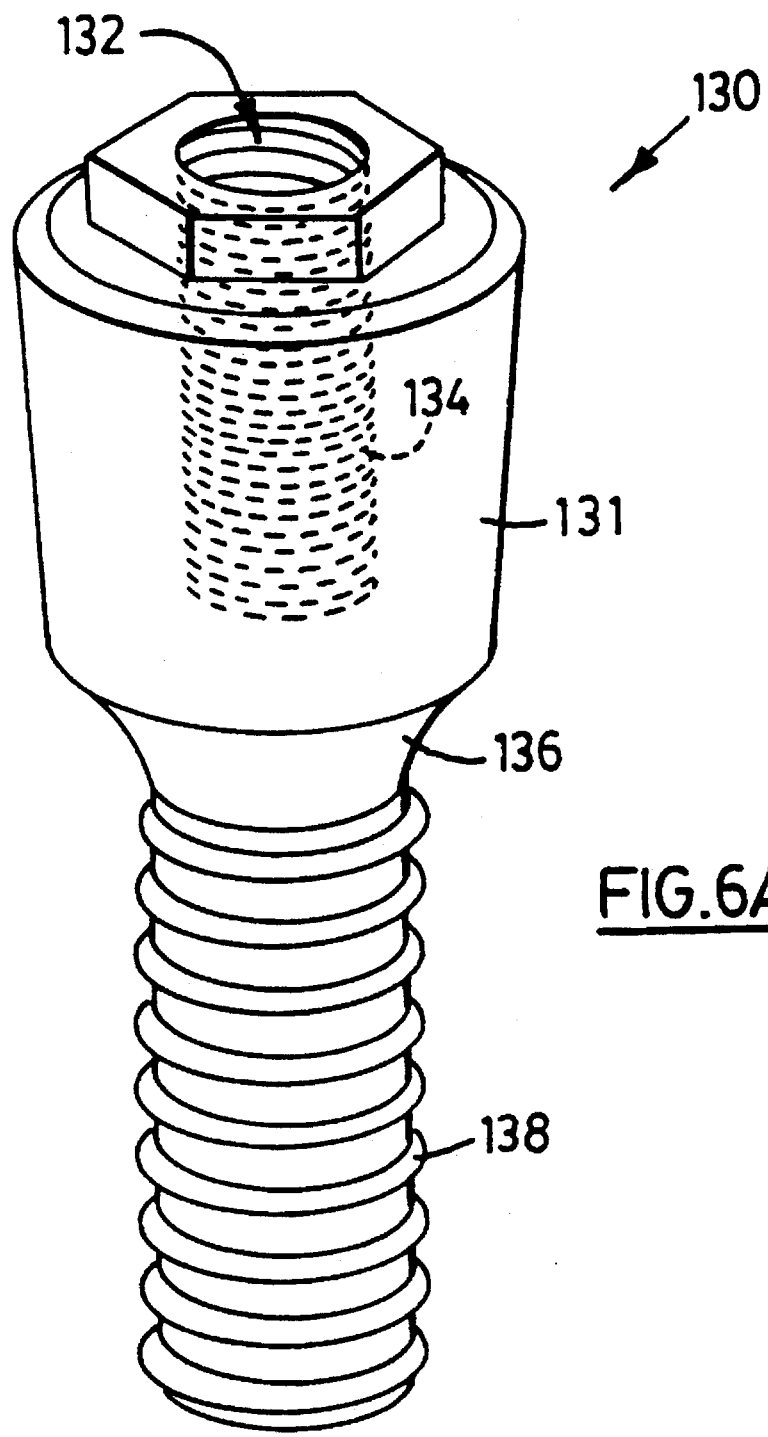
FIG. 6A is a perspective view of an abutment retaining screw which can be used with the abutment of this invention.

Referring to FIG. 6A, it will be seen that retaining screw 130 is comprised of an internal bore 132 with internal threads 134 adapted to receive and engage with the external threads on a multiplicity of dental prostheses (not shown).

The retaining screw 130 is comprised of tapered section 136 which is adapted to fit within bore 63 (see FIG. 2) and mesh with the tapered section therein.

The retaining screw 130 is also comprised of external threads which, after they pass through abutment 10, may be secured to internal threads (not shown) in the implant fixture (not shown in FIG. 6A).

FIG. 6B is an exploded perspective view illustrating that, after retaining screw 130 is passed through abutment 10, it may be screwed into orifice 140 of implant fixture 114 and become screwably engaged with the internal threads located within orifice 140.

In the preferred embodiment illustrated in FIG. 6B, implant fixture 114 is comprised of external threads 142 which can be used to secure implant assembly within the jawbone of a patient.

FIG. 7 is an exploded view showing the abutment 10/retaining screw 130/implant fixture 114 assembly 150 disposed beneath a socket wrench 152 with a hexagonal bore 154. As will be apparent to those skilled in the art, socket wrench 152 may be removably attached to the substantially hexagonal portion 24 of abutment 10 and used to insert assembly 150 into a hole in the patient's jaw. Alternatively, or additionally, depending upon the amount of force needed, carrier 90 may be used for this purpose or, alternatively, to start the insertion of the assembly 150 in said hole.

In the embodiment illustrated in FIG. 7, the implant fixture has an exterior hexagonal shape; and thus it is adapted to be screwed into the hole in the patient's jaw by a socket wrench with a matching hexagonal bore. It will be apparent, however, that the means of inserting the assembly 150 into the hole in the patient's jaw will vary with the type of implant 114 used. Thus, for example, when the exterior shape of implant 114 is substantially cylindrical, a seating tool (such as a mallet) may be used. These procedures are well known to those skilled in the art.

Figure 8:
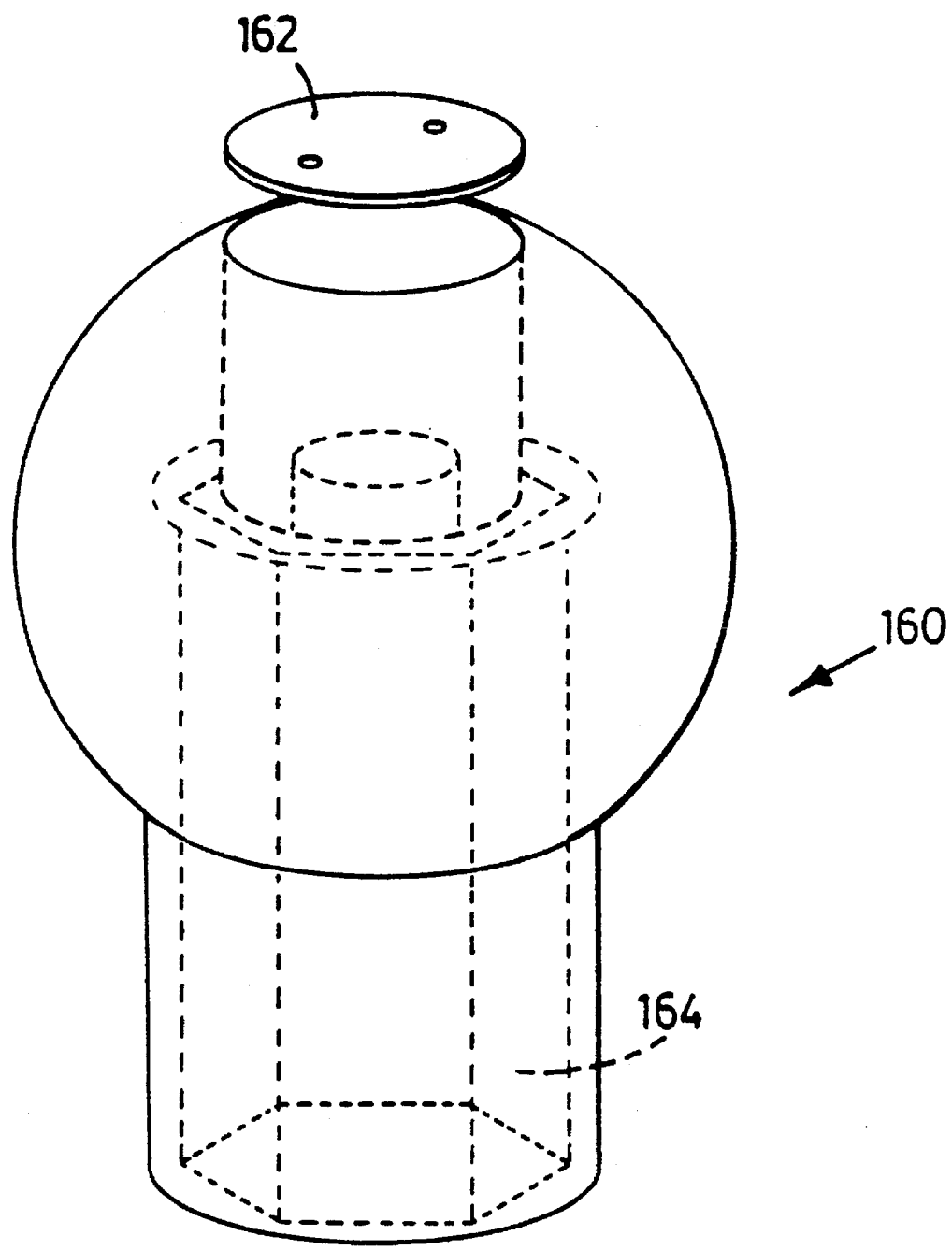
FIG. 8 is view of a healing abutment which is adapted to fit over the hexagonal abutment of FIG. 1.

FIG. 8 is a perspective view of a healing ball 160 which may be used in connection with abutment 10. Referring to FIG. 8, it will be seen that healing ball 160 is comprised of a removable cover 162.

Healing ball 160 preferably consists essentially of medical grade material such as, e.g., medical grade polyethylene. In one preferred embodiment, healing ball 160 consists essentially of high density polyethylene.

Figure 9:
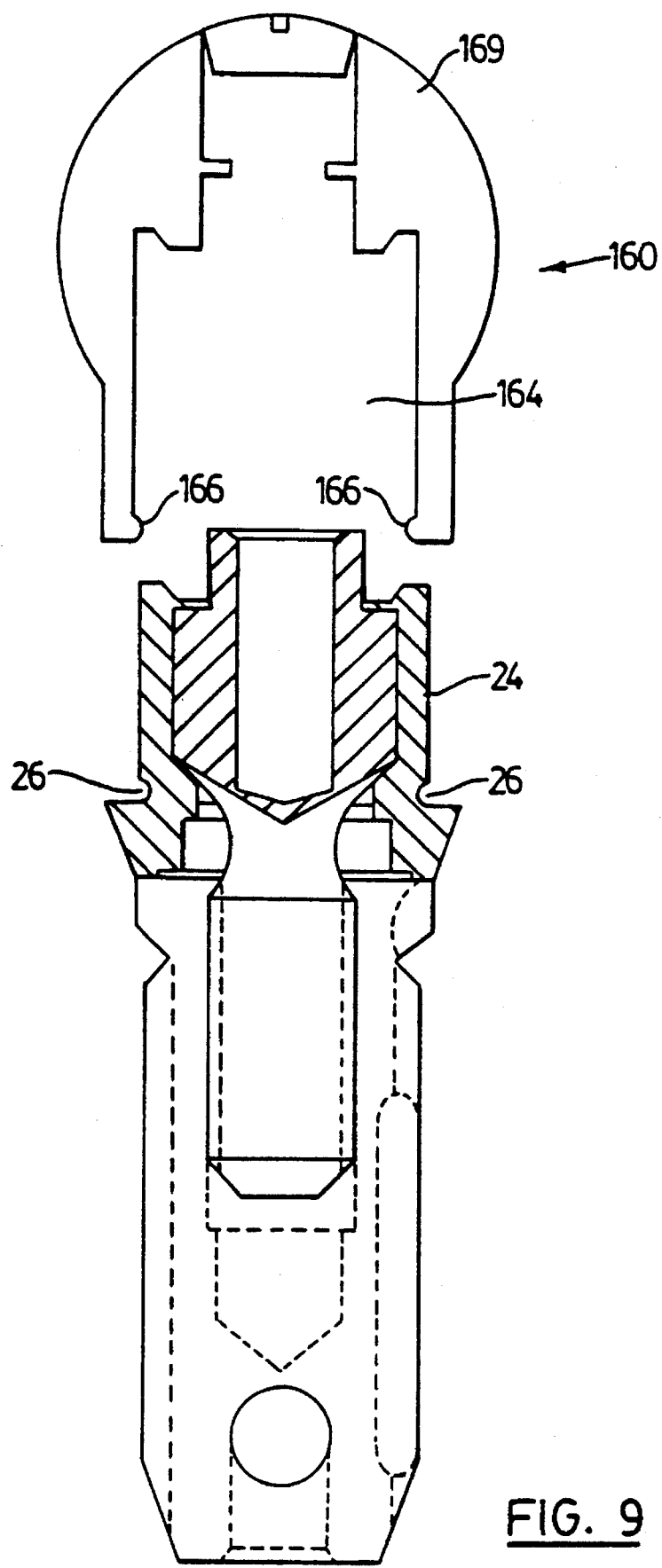
FIG. 9 is a sectional view of the healing abutment connected to applicant's abutment/implant system.

Referring again to FIG. 8, it will be seen that healing ball 160 is comprised of an internal bore 164 which has a substantially hexagonal shape and is adapted to fit snugly over the substantially hexagonal portion 24 of abutment 10 (see FIG. 9).

Referring to FIG. 9, and in the preferred embodiment illustrated therein, it will be seen that healing ball 160 preferably is comprised of an inwardly-extending annular protuberance 166 which is adapted to fit within and removably secured to annular groove 26. There thus is a strong fit between the mating hexagonal portions and the mating annular portions of healing ball 160 and abutment 10.

In many cases, the healing abutment ball 160 is removed from abutment 10 prior to the time any dental device is attached. In some instances, however, it is desired to attach the dental device directly to the healing ball 160. In this latter case, it is sometimes desirable to more securely attach the healing ball 160 to the abutment 10.

Figure 9A:
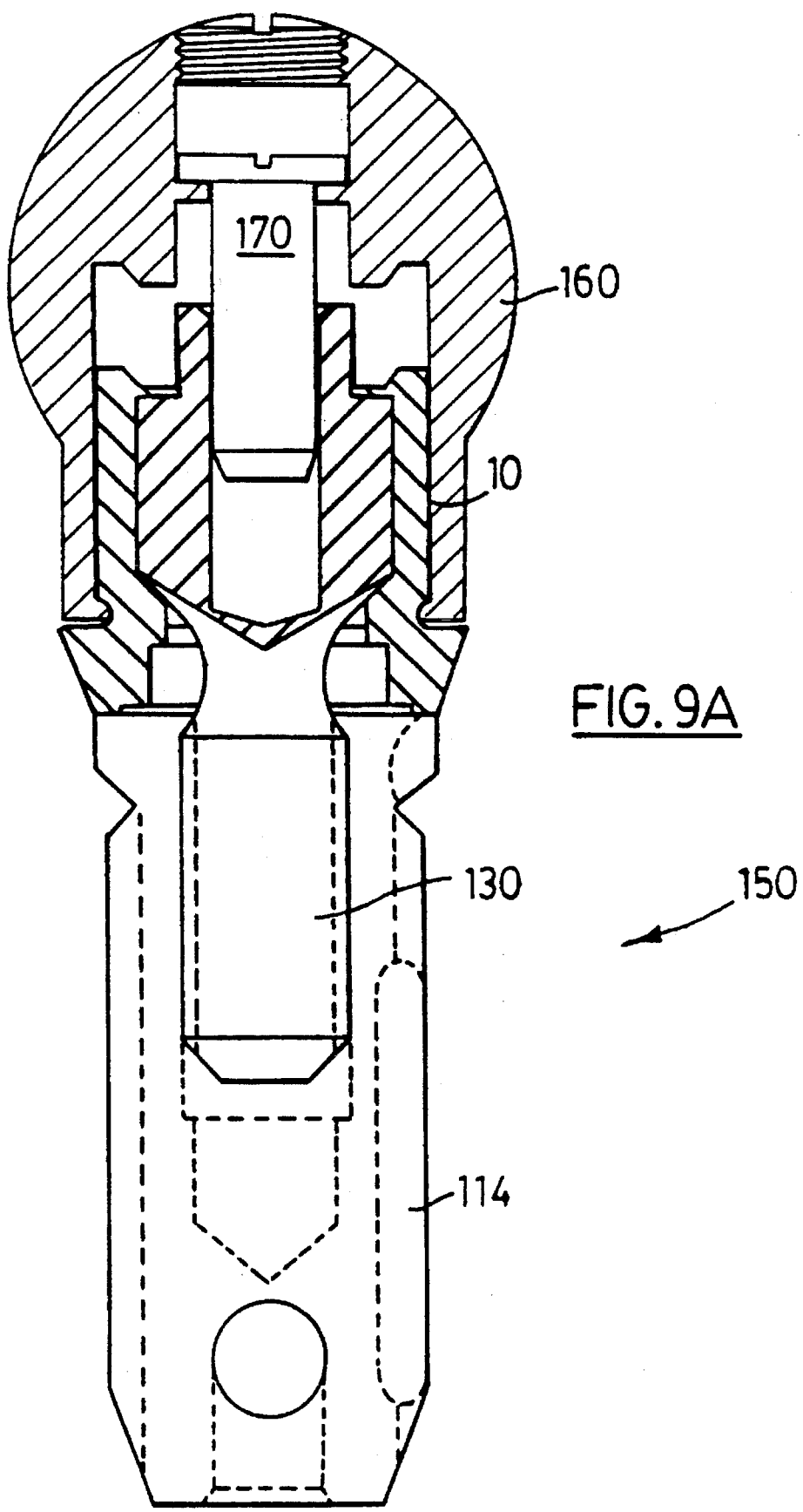
FIG. 9A is a sectional view illustrating another embodiment of the healing abutment connected to applicant's abutment/implant system.

One means of more securely making such attachment is illustrated in FIG. 9A. Referring to FIG. 9A, it will be seen that a screw 170 may be inserted through healing ball 160 into abutment retaining screw 130.

Figure 10:
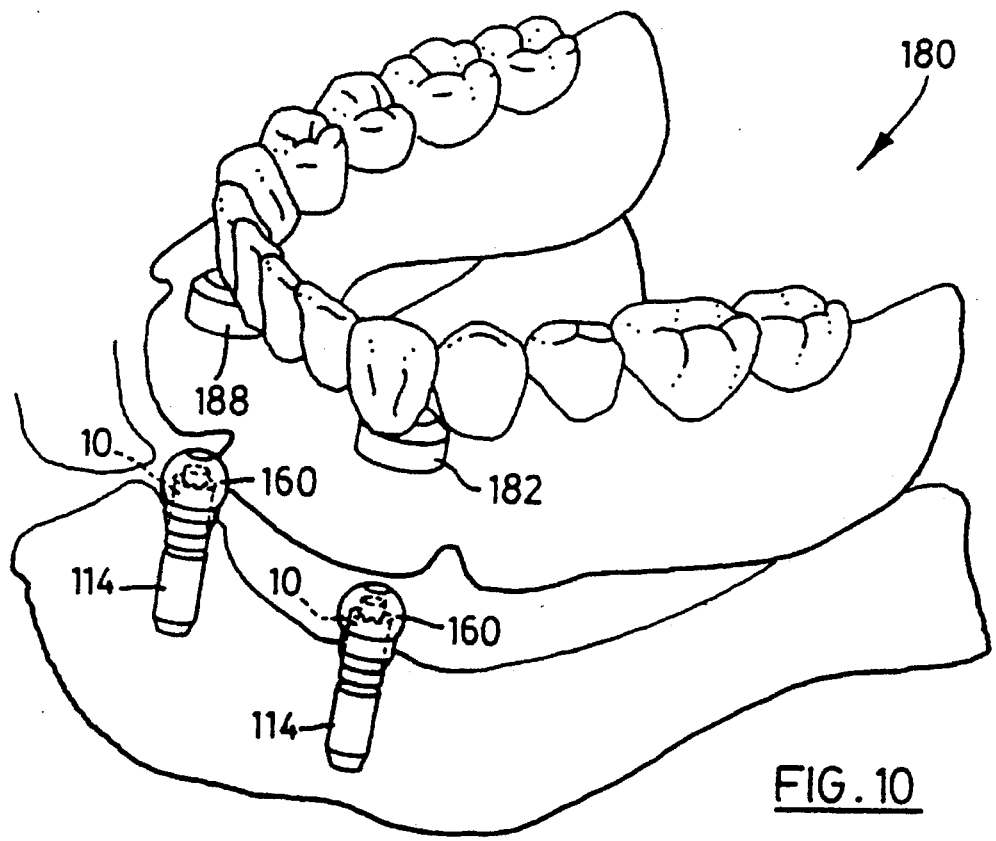
FIG. 10 is a perspective view of a denture connected to the healing abutment/abutment/implant system of FIG. 9 by means of O-rings.

FIG. 10 illustrates a denture 180 into which two metal rings 182 and 184 with O-rings 186 and 188 have been cured into the denture chairside. Such dentures are well known to those skilled in the art and are illustrated on page 21 of the aforementioned Nobelpharma catalog. Furthermore, Nobelpharma also sells an "Overdenture Kit for Ball Attachment" (see page 21 of the catalog) which contains a plastic cap with a rubber O-ring, ball attachment replicas, and spacers for the ball attachment.

Referring again to FIG. 10, it will be seen that the metal ring/O-ring assemblies are friction fit over the healing balls 160 to firmly and securely removably attach the denture 180 to the implant assembly.

FIG. 11 illustrates how the implant assembly 150 may be used in a similar manner with a gold cylinder 190. Such a gold cylinder is well known to those skilled in the art. See, for example, U.S. Pat. No. 5,209,659 (gold cylinder 126), U.S. Pat. No. 5,108,288 (coping 50 having a bore 52 passing axially therethrough and opening into a polygonal opening at its lower end), U.S. Pat. No. 5,145,371, and the like. The disclosure of each of these United States patents is hereby incorporated by reference into this specification.

Figure 12:
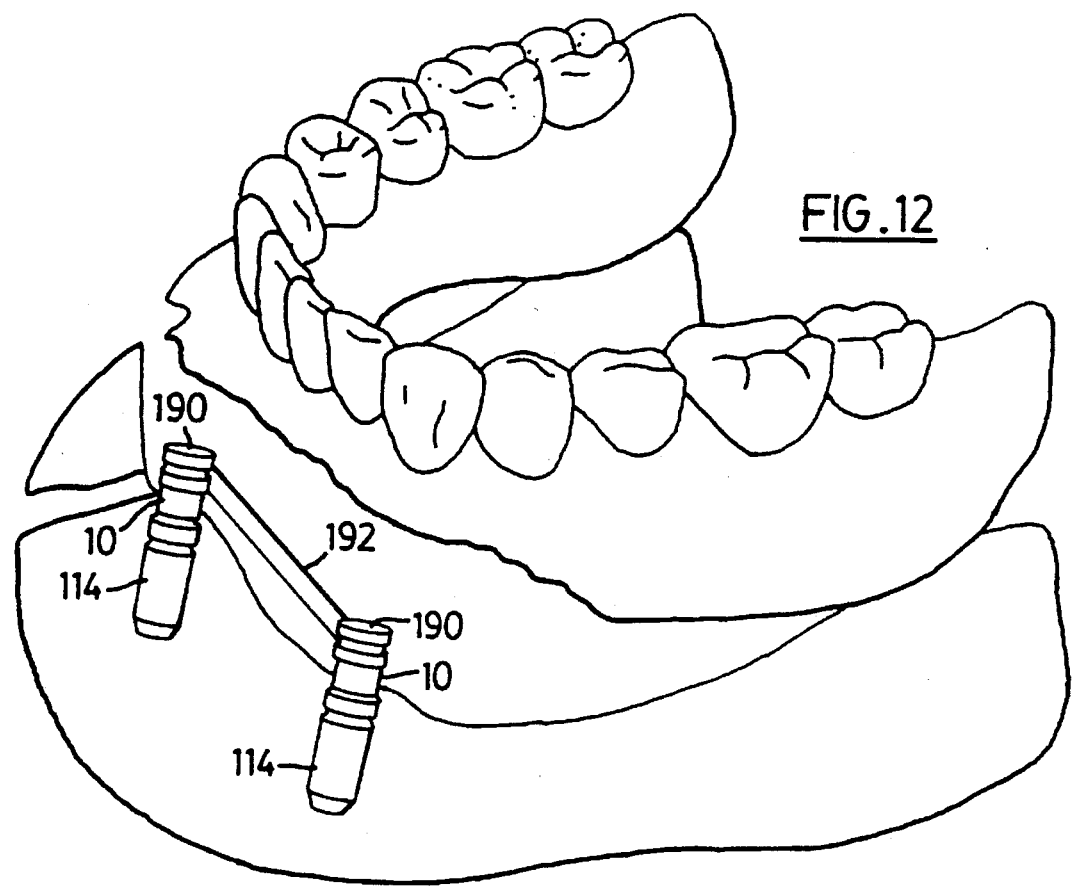
FIG. 12 is a perspective view of the assembly of FIG. 11 connected via a bar and clip to a denture in a patient's mouth.

It is known that gold cylinders are available for the fabrication of bar/clip overdentures, for they are designed to fit accurately on the hex abutments and can be incorporated into the bar/clip framework; see FIG. 12, and the bar clip assembly 192 illustrated therein. As will be apparent to those skilled in the art, this type of over-denture bar system may be readily connected to implant assemblies 150 attached to gold cylinders 190 (see FIG. 11).

Thus, as will be apparent to those skilled in the art, applicant's abutment 10, because of the relative universality of its design, may be used in conjunction with many different types of prosthetic applications. It thus affords the dental practitioner substantially more flexibility than does the prior art systems, which utilize a substantial number of parts which are adapted for specific applications.

Figure 13:
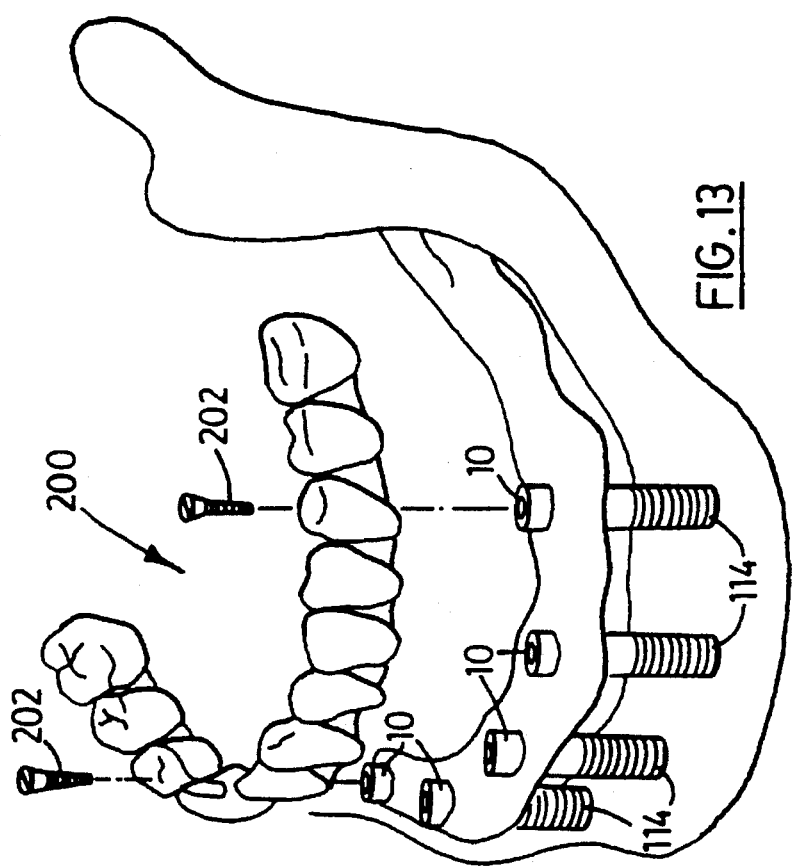
FIG. 13 is a perspective view of a fixed detachable implant supported bridge which utilizes applicant's abutment system.

Thus, by way of further illustration, and referring to FIG. 13, the gold cylinder devices 190 may be incorporated into a fixed detachable implant supported bridge 200. See, e.g., U.S. Pat. No. 5,174,954, the entire disclosure of which is hereby incorporated by reference into this specification.

Referring again to FIG. 13, it will be seen that screws 202 may be used to secure the bridgework through the gold cylinders to the abutments 10.

Figure 14:
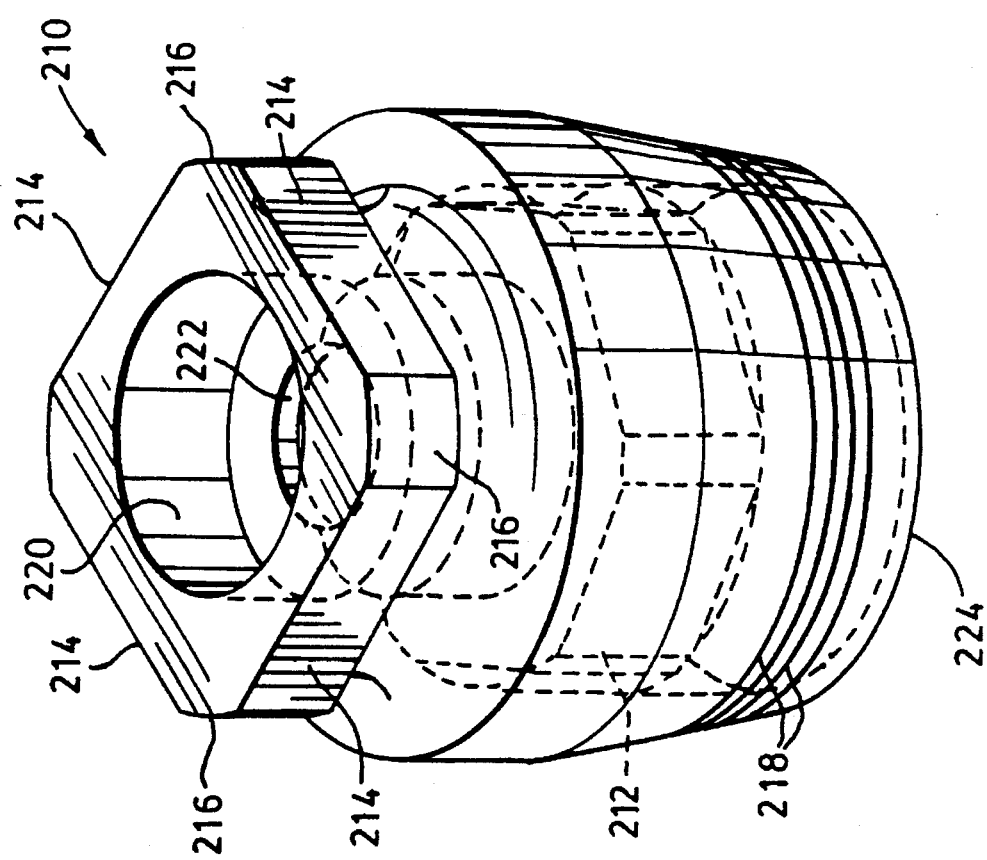
FIG. 14 is a perspective view of a gold coping device which may be used with applicant's abutment system.

FIG. 14 is a perspective view of a gold coping 210 which may be utilized to restore a tooth to a patient's mouth. Referring to FIG. 14, it will be seen that gold coping 210 is comprised of an internal hexagonal bore 212 adapted to fit over and engage with hexagonal portion 24 of abutment 10 (see FIG. 15). As will be apparent to those skilled in the art, when gold coping 210 is placed on abutment 10, there are only six positions it can be in. By comparison, with prior art abutments which have cylindrical outer surfaces, there are an infinite number of such positions.

This system thus has several advantages. Because the gold coping 210/abutment 10 connection is locked into place by the interaction of the hexagonally-shaped parts, a patient cannot cause the tooth attached to abutment 10 to rotate upon application of pressure to the tooth. In the second place, the gold coping 210 can be utilized as a transfer coping during impression taking and, when so used, because of the interaction of the hexagonal shapes, accurately reproduces the position of abutment 10 in the working model.

Referring again to FIG. 14, it will be seen that, in the preferred embodiment illustrated therein, gold coping 210 has a substantially rectiliner top shape 214 with rounded corners 216. In one embodiment, the top of gold coping 210 is substantially square-shaped with rounded corners.

Referring again to FIG. 14, it is preferred that gold coping 210 comprise a multiplicity of annular grooves 218. Gold coping 210 also is comprised of stepped bores 220 and 222.

The gold copying 210 preferably consist essentially of a palladium alloy such as, e.g., the alloy disclosed in U.S. Pat. No. 5,174,954, the entire disclosure of which is hereby incorporated by reference into this specification. Thus, e.g., one may use a palladium alloy containing from about 50 to about 90 weight percent of palladium, from about 0 to about 37 weight percent of gold, from about 0 to about 3 weight percent of platinum, from about 0 to about 35 weight percent of silver, from about 0.5 to about 8 weight percent of gallium, from about 0 to about 8 weight percent of tin, and up to about 0.2 weight percent of a material selected from the group consisting of iridium, rhenium, ruthenium, and mixtures thereof.

Referring again to FIG. 14, it is preferred that the bottom portion 224 of gold coping 210 be adapted to mesh with a fit onto ledge 22 of abutment 10 (see FIG. 1).

Figures 15, 16:
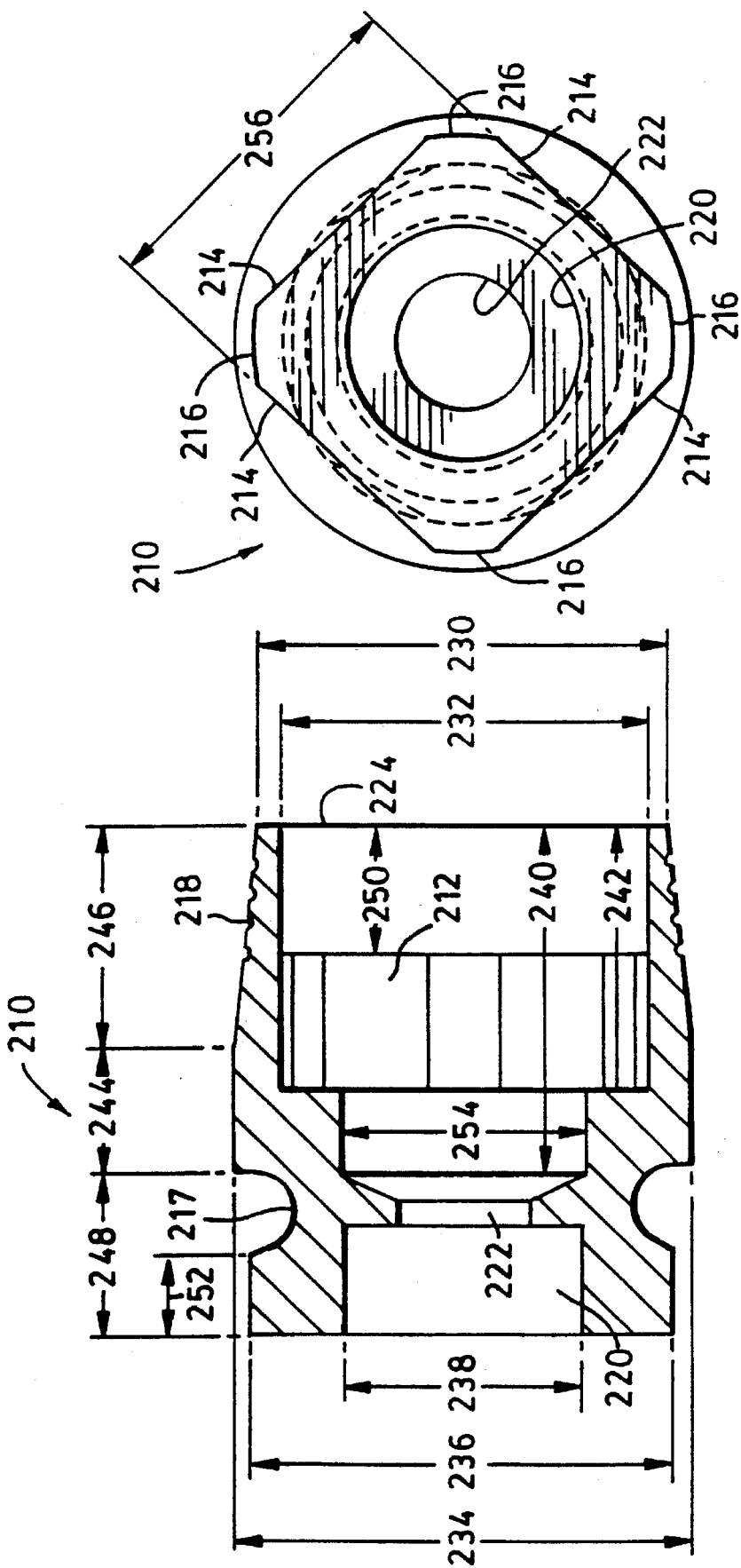
FIG. 15 is a sectional view of the gold coping device of FIG. 14.
FIG. 16 is a top view of the gold coping device of FIG. 14.

FIG. 15 is a sectional view of the gold coping device of FIG. 14. Referring to FIG. 15, and also to FIG. 14, it will be seen that gold coping 210 is comprised of a curved neck portion with a radius of curvature of about 1.5 millimeters.

In the preferred embodiment illustrated in FIG. 15, it will be seen that distance 230 is preferably 4.7 millimeters, distance 232 is preferably 4.2 millimeters, distance 234 is preferably 5.2 millimeters, distance 236 is 4.6 millimeters, distance 238 is 2.7 millimeters, distance 240 is 4.1 millimeters, distance 242 is 3.1 millimeters, distance 244 is 1.5 millimeters, distance 246 is 2.5 millimeters, distance 248 is 2 millimeters, distance 250 is 1.5 millimeters, and distance 252 is 1.5 millimeters, and distance 254 is 2.8 millimeters.

FIG. 16 is a top view of the gold coping of FIG. 14. Referring to FIG. 16, it will be seen that the distance 256 from opposing flat surfaces 214 is 4.0 millimeters.

FIG. 17 is an exploded perspective view illustrating how a tooth to which a gold coping 210 has been bonded may be attached to a patient's jawbone (not shown) by means of the abutment system of this invention.

Referring to FIG. 17, and in the preferred embodiment depicted, it will be seen that tooth 270 may be secured to abutment 10 by at least two separate means.

In the first place, a screw 272 may be inserted through orifice 22 and secured to retaining screw 130 by engagement with internal threads 134 (not shown in FIG. 17, but see FIG. 6A).

In the second place, dental cement may be charged into the interior of gold coping 210 prior to the time the gold coping 210 is placed over the hexagonal portion 24 of abutment 10. Thus, in addition to the mechanical bond created by screw 272, there also is an adhesive bond.

Furthermore, there is yet another bond tending to maintain gold coping 210 in position vis-a-vis abutment 10, and that is the interaction of their respective hexagonal shapes.

The system depicted in FIG. 17 has the unique advantage that allows the removal of the tooth 270 from the abutment 10 even after the cement has hardened. In order to do this, screw 272 may be removed by turning it counterclockwise, and thereafter, utilizing a three-pronged crown-remover to pull tooth 270 out of the abutment 10 by leverage between the top of retaining screw 130 against the smaller taper of 270.

A preferred process of the invention

Figure 18:
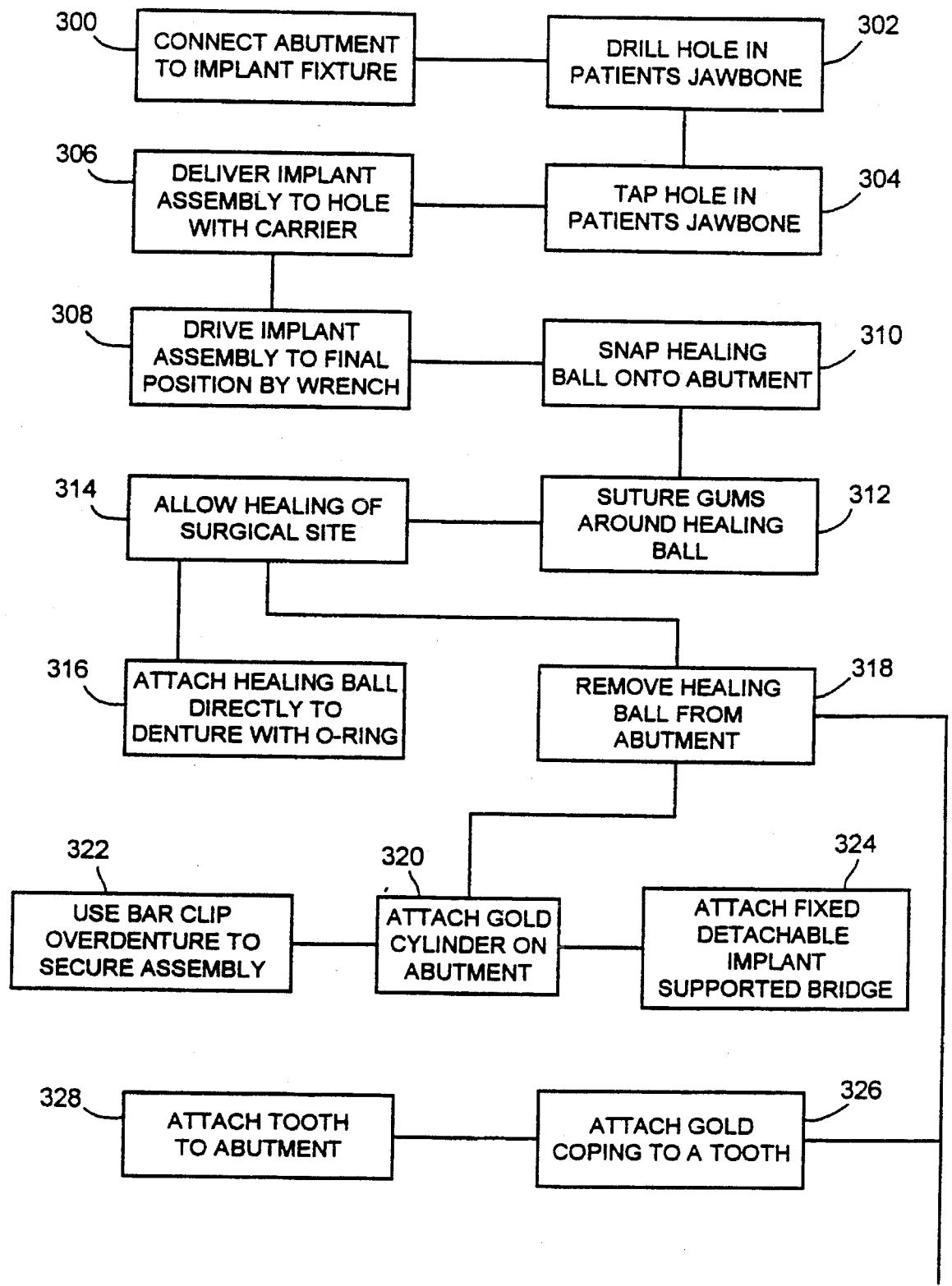
FIG. 18 a flow diagram illustrated certain preferred processes of the invention.

FIG. 18 is a flow diagram of one preferred process of applicant's invention.

In the first step of this process, step 300, abutment 10 is connected to implant fixture 114.

In this step, it is preferred to apply a torque no greater than about 20 Newton/centimeter.

Thereafter, in step 302 of the process, a hole is drilled in the jawbone of the patient sufficiently deep to receive only the length of the implant fixture. In general, this hole is usually from about 8 to about 18 millimeters.

Thereafter, in step 304 of the process, the hole thus drilled is preferably tapped with a tapping tool such as, e.g., the screw taps illustrated on page 11 of the Nobelpharma catalog.

Thereafter, in step 306 of the process, the abutment/implant fixture assembly is delivered to the hole by means of the carrier 90. The carrier 90 may also be used to start screwing the assembly into the hole, applying downward pressure while turning the assembly.

Generally, the carrier 90 will only enable one to drive the abutment/implant fixture assembly a portion of the required distance. The job may be finished by a power-driven socket wrench in step 308 of the process In the next step of this preferred process, step 310, the healing ball 160 is preferably snapped onto the abutment 10 (see FIGS. 9 and 9A). In one preferred embodiment, the healing ball 160 is disposed within compartment 101 of carrier 90 prior to its use.

Thereafter, in step 312, the gum tissue where the hole had been drilled is sutured around the healing ball 160.

In the next step of process, step 314, the surgical site is allowed to heal before the abutment 10 is directly or indirectly connected to a denture. In general, a healing period of from about 3 to about 6 months is desirable.

After the desired time of healing, no additional surgical procedure is required, unlike the prior art process (which necessitated second stage surgery to remove the cover screw used in the process and to attach the prosthetic abutment). By comparison with prior art processes, applicant's prosthetic abutment is already attached.

At this stage of applicant's process, several options are available.

In one embodiment, illustrated in step 316 (also see FIG. 10), the healing ball is attached directly to a denture into which metal caps with an O-ring have been cured.

In another embodiment, illustrated in step 318, the healing ball 160 is removed from the abutment 10. At this stage, several additional options are available.

One such option is to attach the gold cylinder 190 on the abutment 10 (see FIGS. 11 and 12) in step 320. Once the gold cylinder 190 has been so attached, one may prepare a bar clip overdenture (see FIG. 12) and attach such denture to the superstructure (see step 322). Alternatively, in step 324, the gold cylinders 190 can be incorporated into a fixed detachable implant supported bridge and thereafter secured to multiple implants in place in the jawbone (see FIG. 13).

Alternatively, in step 326, after the healing ball 160 has been removed a gold coping 210 may be attached to a tooth (see, e.g., FIG. 17 where such a gold coping is imbedded in the tooth). Thereafter, in step 328, such tooth is attached to the abutment 10.

It is to be understood that the aforementioned description is illustrative only and that changes can be made in the apparatus, in the ingredients and their proportions, and in the sequence of combinations and process steps, as well as in other aspects of the invention discussed herein, without departing from the scope of the invention as defined in the following claims.

I claim:

1. A dental implant assembly comprised of an integrally-formed abutment, wherein said abutment is comprised of a top section, a bottom section integrally joined to said top section, and a passageway extending through said top section and said bottom section, and wherein:
   (a) said passageway is formed from a first stepped bore, a second stepped bore, a third stepped bore, a fourth stepped bore, a fifth stepped bore, and a sixth stepped bore, wherein:
      i. said first stepped bore is adjacent to and is larger than said second stepped bore,
      ii. said second stepped bore is adjacent to and is larger than said third stepped bore,
      iii. said third stepped bore is adjacent to and is larger than said fourth stepped bore,
      iiii. said fourth stepped bore is adjacent to and is smaller than said fifth stepped bore, and
      iiiii. said fifth stepped bore is adjacent to and is smaller than said sixth stepped bore,
   (b) said top section has a cross-sectional shape substantially like a polygon, wherein said shape is formed by alternating linear and arcuate walls.

2. The dental implant assembly as recited in claim 1, wherein an arcuate inwardly-extending groove is disposed between said top section and said bottom section of said abutment.

3. The dental implant assembly as recited in claim 1, wherein said top section has a cross-section shape substantially like a hexagon.

4. The dental implant assembly as recited in claim 3, wherein said abutment consists essentially of titanium.

5. The dental implant assembly as recited in claim 3, wherein said abutment consists essentially of titanium alloy.

6. The dental implant assembly as recited in claim 2, wherein said abutment is comprised of a horizontally-extending ledge disposed beneath said top section of said abutment.

7. The dental implant assembly as recited in claim 3, wherein said hexagonal shape is defined by six substantially equal linear sections and six substantially equal arcuate sections.

8. The dental implant assembly as recited in claim 7, wherein each of said substantially equal linear sections is at least three times as long as each of said substantially equal arcuate sections.

9. The dental implant assembly as recited in claim 6, wherein said abutment is comprised of a base.

10. The dental implant assembly as recited in claim 9, wherein said base extends upwardly and outwardly from its bottom to its top.

11. The dental implant assembly as recited in claim 1, wherein said sixth stepped bore has a cross-sectional shape of a hexagon.

12. The dental implant assembly as recited in claim 1, wherein said first stepped bore is defined by an inwardly-extending chamfered surface.

13. The dental implant assembly as recited in claim 1, wherein said third stepped bore is defined by an inwardly-extending chamfered surface.

14. The dental implant assembly as recited in claim 1, wherein said implant assembly further comprises a retaining screw disposed within said first stepped bore, said second stepped bore, said third stepped bore, said fourth stepped bore, said fifth stepped bore, and said sixth stepped bore.

15. The dental implant assembly as recited in claim 14, wherein said retaining screw is comprised of a seventh bore comprising an interior threaded surface.

16. The dental implant assembly as recited in claim 15, wherein said retaining screw is attached to an implant fixture.

17. The dental implant assembly as recited in claim 16, wherein a fastener is removably attached within said seventh bore of said retaining screw.

* * * * *